(12) United States Patent
Edwards

(10) Patent No.: US 9,463,330 B2
(45) Date of Patent: *Oct. 11, 2016

(54) DELIVERY OF SKIN CARE PRODUCTS

(75) Inventor: Jeffrey D. Edwards, Perth (AU)

(73) Assignee: INTERNATIONAL SCIENTIFIC PTY LTD, Leederville, Western Australia (AU)

( * ) Notice: Subject to any disclaimer, the term of this patent is extended or adjusted under 35 U.S.C. 154(b) by 222 days.

This patent is subject to a terminal disclaimer.

(21) Appl. No.: 13/704,157

(22) PCT Filed: Jun. 17, 2011

(86) PCT No.: PCT/AU2011/000735
§ 371 (c)(1),
(2), (4) Date: Feb. 25, 2013

(87) PCT Pub. No.: WO2011/156869
PCT Pub. Date: Dec. 22, 2011

(65) Prior Publication Data
US 2013/0144109 A1 Jun. 6, 2013

(30) Foreign Application Priority Data
Jun. 17, 2010 (AU) ................ 2010902650

(51) Int. Cl.
*A61N 2/00* (2006.01)
*A61M 37/00* (2006.01)

(52) U.S. Cl.
CPC .............. *A61N 2/002* (2013.01); *A61M 37/00* (2013.01); *A61M 2037/0007* (2013.01)

(58) Field of Classification Search
CPC .................... A61M 2037/0007; A61M 37/00; A61N 2/002
See application file for complete search history.

(56) References Cited

U.S. PATENT DOCUMENTS

| | | |
|---|---|---|
| 4,079,038 A | 3/1978 | Choi et al. |
| 4,093,709 A | 6/1978 | Choi et al. |
| 4,131,648 A | 12/1978 | Choi et al. |
| 4,138,344 A | 2/1979 | Choi et al. |
| 4,180,646 A | 12/1979 | Choi et al. |
| 4,304,767 A | 12/1981 | Heller et al. |

(Continued)

FOREIGN PATENT DOCUMENTS

| | | |
|---|---|---|
| AT | 7445 U2 | 4/2005 |
| JP | 49-145870 | 3/1948 |

(Continued)

OTHER PUBLICATIONS

International Search Report and Written Opinion of the International Searching Authority issued in connection with International Application No. PCT/AU2011/000735, dated Aug. 22, 2011.

(Continued)

*Primary Examiner* — Imani Hayman
(74) *Attorney, Agent, or Firm* — Marshall, Gerstein & Borun LLP

(57) ABSTRACT

A method for the delivery of a skin care active agent comprising the following step: applying an active agent(s) between a target dermal barrier and a magnetic device comprising one or more pairs of displaced dipolar magnetic elements linked by a magnetic return wherein the magnetic return is orientated on the surfaces of the dipole pair distal to the dermal barrier.

12 Claims, 16 Drawing Sheets

(56) References Cited

U.S. PATENT DOCUMENTS

| | | | |
|---|---|---|---|
| 4,502,497 A | 3/1985 | Siahou | |
| 4,571,768 A | 2/1986 | Kawashima | |
| 4,946,931 A | 8/1990 | Heller et al. | |
| 5,785,956 A | 7/1998 | Sullivan et al. | |
| 5,800,685 A | 9/1998 | Perrault | |
| 5,968,543 A | 10/1999 | Heller et al. | |
| 6,338,751 B1 | 1/2002 | Litkowski et al. | |
| 6,383,129 B1* | 5/2002 | Ardizzone | A61N 2/06 600/15 |
| 6,413,536 B1 | 7/2002 | Gibson et al. | |
| 6,596,296 B1 | 7/2003 | Nelson et al. | |
| 6,613,355 B2 | 9/2003 | Ng et al. | |
| 6,631,294 B2 | 10/2003 | Andino et al. | |
| 6,667,371 B2 | 12/2003 | Ng et al. | |
| 6,845,272 B1 | 1/2005 | Thomsen et al. | |
| 2003/0172482 A1* | 9/2003 | Tini | 15/167.1 |
| 2005/0255427 A1* | 11/2005 | Shortt et al. | 433/118 |
| 2007/0208209 A1 | 9/2007 | Holcomb | |
| 2009/0093669 A1 | 4/2009 | Farone et al. | |
| 2010/0212676 A1 | 8/2010 | Shapiro et al. | |

FOREIGN PATENT DOCUMENTS

| | | |
|---|---|---|
| JP | 59-149480 | 4/1953 |
| JP | 5046200 | 4/1976 |
| JP | 60-88825 | 6/1986 |
| JP | 61-196756 | 12/1986 |
| JP | 62-15354 | 1/1987 |
| JP | 1-30200 | 9/1989 |
| JP | 06-014813 | 1/1994 |
| JP | 10-192419 | 7/1998 |
| JP | H11113638 A | 4/1999 |
| JP | 2008521514 | 6/2008 |
| WO | WO-2000/023144 A1 | 4/2000 |
| WO | WO-2009/135246 A1 | 11/2009 |

OTHER PUBLICATIONS

Duckworth et al., Fluoride uptake to demineralised enamel: a comparison of sampling techniques, Caries Res., 32:417-21 (1998).

Shi et al., Rapid method for the determination of trace fluoride and activation of ion-selective electrode, Anal. Sci., 19(5):671-3 (2003).

* cited by examiner

DELIVERY OF SKIN CARE PRODUCTS

CROSS-REFERENCE TO RELATED APPLICATIONS

This application is the U.S. national stage of International Application No. PCT/AU2011/000735, filed Jun. 17, 2011, incorporated herein by reference, which claims priority benefit of Australian Patent Application No. 2010902650, filed Jun. 17, 2010.

FIELD OF THE INVENTION

The present invention relates to a method and apparatus for enhanced delivery of substances (such as pharmaceuticals, nutraceuticals, biopharmaceuticals, cosmeceutical, colouring agents, fillers, plumping agents, biologically active substances, anti-inflammatory agents, anti-aging agents, anti-wrinkle agents, moisturisers, humectants, detergents, cleaners, bleaches, dyes, fragrances, conditioners or polishes) to the skin and other components of the integumentary system by application of magnetic fields having distinctive, complex characteristics when such magnetic fields are stationary or in motion.

BACKGROUND ART

The delivery of active agents to or into the skin and other biological components of the body must occur in sufficient amounts to allow the agent to achieve its purpose. However it can be difficult to achieve sufficient delivery of agents to and through various biological barriers due to difficulties in maintaining sufficient concentration in the operational environment and to the permeability barrier effect of many target biological barriers found in the integument system.

Furthermore, there is a general push, due to economic, health-related and environmental reasons, to use less of many active agents in a given composition. This provides further problems in relation to the delivery of active agents, as there may not be a sufficient concentration gradient to allow the active agent to diffuse effectively and to penetrate or partition into barriers such as the skin.

Chemical penetration enhancers can facilitate changes in barrier permeability. However, the use of chemical penetration enhancers can be problematic due to unknown interaction with the active agent and the potential for adverse side effects such as irritation of skin and mucosal surfaces or unwanted interactions with the cosmetic and or functional properties of barriers.

A diffusion enhancement technique which may be used for some biological surfaces is iontophoresis, in which an electrical energy gradient is used to accelerate the charged target active agent(s) across the skin or barrier. However, iontophoresis is only suitable to specific active agents with certain ionic structures and can be injurious to certain dermal barriers due to exchange ion degradation. Additionally, iontophoresis requires the use of intimate electrical contact and adhesive electrodes, which are not suitable for all target surfaces or barriers.

Other techniques to create mobility and/or direction in the movement of active agent(s) such as magnetokinetics and magnetophoresis are possible, however they have been difficult to implement due to poor performance, high hardware and energy requirements, and cost.

There is therefore a need for methods to enhance the availability, diffusion characteristics and penetration of active agents into biological barriers such as skin using physical technologies which can replace or at least compliment the previously known chemical and physical penetration enhancers.

The present invention seeks to provide an improved delivery process for active agents that have a pharmaceutical, nutraceutical, biopharmaceutical, cosmeceutical, colouring, filling, plumping, anti-inflammatory, anti-aging, anti-wrinkle agents, moisturising, humectant, detergent, cleansing, bleaching, dye, fragrance, conditioning, anti-bacterial, anti-viral, antifungal, anti-parasitic, activity in a manner which increases the penetration of these agents into various biological barriers such as skin and other tissues of the integumentary system.

The previous discussion of the background art was intended to facilitate an understanding of the present invention only. The discussion is not an acknowledgement or admission that any of the material referred to is or was part of the common general knowledge as at the priority date of the application.

SUMMARY OF THE INVENTION

In accordance with a first aspect of the present invention, there is provided a method for the delivery of a skin care active agent(s) comprising the following step:
(a) applying an active agent(s) between a target dermal barrier and a magnetic device comprising one or more pairs of displaced dipolar magnetic elements linked by a magnetic return wherein the magnetic return is orientated on the surfaces of the dipole pair distal to the dermal barrier.

In accordance with a second aspect of the invention, there is provided a method for the delivery of a skin care active agent(s) comprising the following steps:
(a) applying an active agent(s) between a target dermal barrier and a magnetic device comprising one or more pairs of displaced dipolar magnetic elements linked by a magnetic return wherein the magnetic return is orientated on the surfaces of the dipole pair distal to the dermal barrier; and
(b) moving in a reciprocal, rotational or orbital manner the magnetic device so that active agents in proximity to said device will be subject to alternating polarities of magnetic flux in response to said reciprocal, rotational or orbital movement.

In accordance with a third aspect of the invention, there is provided a method for the delivery of a skin care active agent(s) comprising the following steps:
(a) applying a active agent(s) between a target dermal barrier and a magnetic device comprising at least two sets of pairs of displaced dipolar magnetic elements linked by a magnetic return wherein the magnetic return is orientated on the surfaces of the dipole pair distal to the dermal barrier and wherein the alignment of the first set of displaced dipolar magnetic elements is angularly offset relative to the alignment of the second set of displaced dipolar magnetic elements.

In accordance with a fourth aspect of the invention, there is provided a method for the delivery of a skin care active agent(s) comprising the following steps:
(a) applying a active agent(s) between a target dermal barrier and a magnetic device comprising at least two sets of pairs of displaced dipolar magnetic elements linked by a magnetic return wherein the magnetic return is orientated on the surfaces of the dipole pair distal to the dermal barrier and wherein the alignment of the first set of displaced dipolar magnetic elements is angularly offset relative to the alignment of the second set of displaced dipolar magnetic elements (b) moving in a reciprocal, rotational or orbital manner the magnetic device so that active agents in proximity to said device will be subject to alternating polarities of magnetic field and alternating magnetic gradients in response to said reciprocal, rotational or orbital movement.

According to a form of the invention the method of the invention provides a means for driving the passage of active agent(s) across a dermal barrier such as the layers of the skin (epidermis, dermis), including the stratum corneum, granular cell layer, spinous cell layer, basal cell layer and other components of the integumentary system into a subject (including a patient). The method may be enhanced by the additional step of pairing the device with an alternate drug delivery system that operates either in conjunction with, or in parallel with, the device, to promote the passage of active agents through the dermal barrier. Such alternate drug delivery systems may include, for example, iontophoresis, drug-adhesive matrix, chemical penetration enhancers, microneedles and sonophoresis.

During performance of the method of the invention, the active agent(s) or a formulation including the active agent(s) is placed between the device and the subject (including a patient).

According to a particular form of the invention, the device is in the form of a brush, with the active agent located on some or all of the bristles of the brush or on the dermal barrier to be brushed.

In another a form of the invention the device comprises a pad or strip within which is located a flexible or inflexible magnetic material. The pad may be reversibly applied or adhered to the dermal barrier to which the active agent(s) is desired to be delivered, or may be rubbed over the skin or and other components of the integumentary system requiring treatment. The active agent(s) may be releasably contained within the pad or may be applied to the dermal barrier prior to application or adhering of the pad to the dermal barrier or rubbing of the pad over the skin.

In another form of the invention, the device may comprise a roller applicator or pen device which can be moved or rubbed, either manually or by motorised action over the dermal barrier. The active agent may be applied to or incorporated in the device prior to it being rubbed over the skin, or the active agent may be applied to the skin prior to the device being rubbed or moved over it.

Other aspects and advantages of the invention will become apparent to those skilled in the art from a review of the ensuing description, which proceeds with reference to the following illustrative drawings.

BRIEF DESCRIPTION OF THE DRAWINGS

The present invention will now be described, by way of example only, with reference to the accompanying drawings.

FIG. 2A is a diagrammatic representation of the magnetic elements. FIG. 2B is a diagrammatic representation of the polarities generated by the magnetic elements. FIG. 2C is a photograph of a magnetic film comprising two sets of displaced dipolar magnetic elements wherein the orientation of the second set is 90° to the orientation of the first set, showing the complex magnetic fields generated by the 90° offset magnetic elements.

FIG. 3A is a diagrammatic representation of the magnetic elements. FIG. 3B is a diagrammatic representation of the polarities generated by the magnetic elements. FIG. 3C is a photograph of a magnetic film comprising two sets of displaced dipolar magnetic elements wherein the orientation of the second set is 45° to the orientation of the first set, showing the complex magnetic fields generated by the 45° offset magnetic elements.

DESCRIPTION OF THE INVENTION

General

Figure 1:
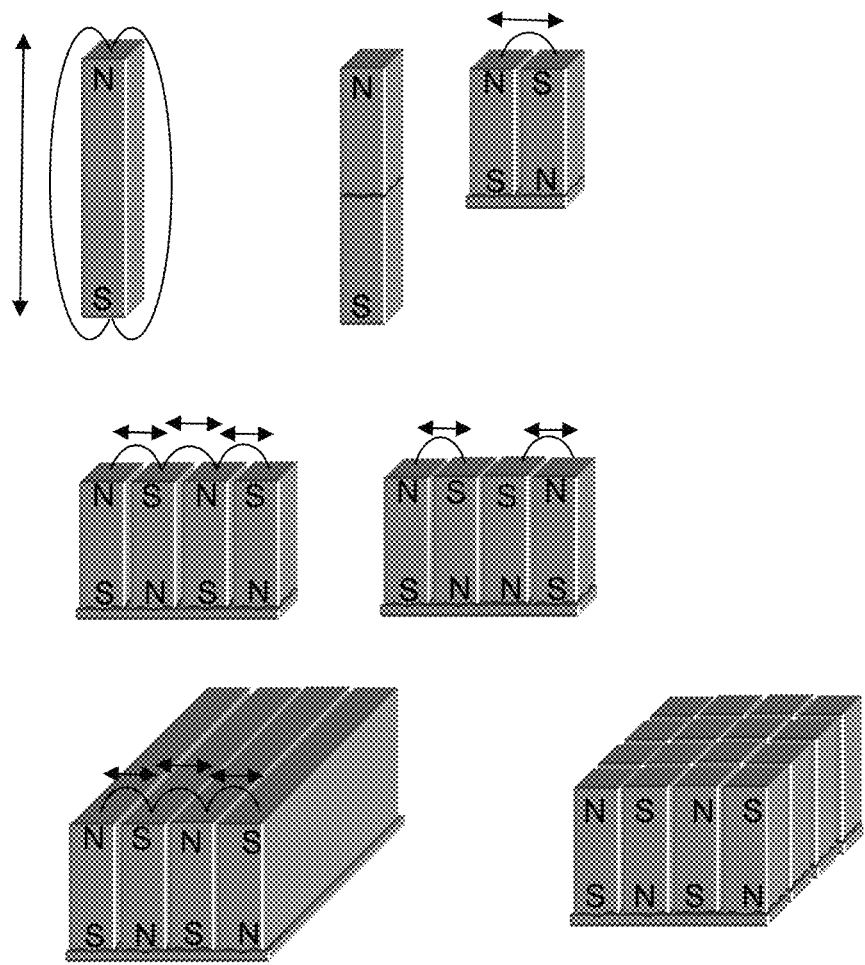
FIG. 1 is a representation of the nature of a pair of displaced dipolar magnetic elements and the magnetic return, and various combinations and orientations of dipole pairs. The arcs drawn between dipole pairs indicate magnetic return.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg. size, displacement and field strength etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Preferred Embodiments

The inventor of the present invention has revealed that the penetration of an active agent into, through or onto the skin or other components of integumentary system can be enhanced by magnetic flux. The inventors of the present invention also reveal that certain arrangements of magnetic flux may induce thermal noise and other forms of molecular disorder, which act against such magnetic enhanced penetration. As a result only specific arrangements of magnetic elements, as disclosed by the present invention, permit the coexistence of diamagnetic repulsion enhanced diffusion of active ingredients and dielectric polarisation enhanced permeation changes of the skin and other components of the integumentary system.

Therefore, in accordance with a first aspect of the present invention, there is provided a method for the delivery of a skin care active agent(s) comprising the following step:
  (a) applying an active agent(s) between a dermal barrier and a magnetic device comprising one or more pairs of displaced dipolar magnetic elements linked by a magnetic return wherein the magnetic return is orientated on the surfaces of the dipole pair distal to the dermal barrier.

In accordance with a second aspect of the invention, there is provided a method for the delivery of a skin care active agent(s) comprising the following steps:
  (a) applying an active agent(s) between a target dermal barrier and a magnetic device comprising one or more pairs of displaced dipolar magnetic elements linked by a magnetic return wherein the magnetic return is orientated on the surfaces of the dipole pair distal to the dermal barrier; and
  (b) moving in a reciprocal, rotational or orbital manner the magnetic device so that active agents in proximity to said device will be subject to alternating polarities of magnetic flux in response to said reciprocal, rotational or orbital movement.

In accordance with a third aspect of the invention, there is provided a method for the delivery of a skin care active agent(s) comprising the following step:
  (a) applying a active agent(s) between a dermal barrier and a magnetic device comprising at least two sets of pairs of displaced dipolar magnetic elements linked by a magnetic return wherein the magnetic return is orientated on the surfaces of the dipole pair distal to the dermal barrier and wherein the alignment of the first set of displaced dipolar magnetic elements is angularly offset relative to the alignment of the second set of displaced dipolar magnetic elements.

In accordance with a fourth aspect of the invention, there is provided a method for the delivery of a skin care active agent(s) comprising the following steps:
  (a) applying a active agent(s) between a target dermal barrier and a magnetic device comprising at least two sets of pairs of displaced dipolar magnetic elements linked by a magnetic return wherein the magnetic return is orientated on the surfaces of the dipole pair distal to the dermal barrier and wherein the alignment of the first set of displaced dipolar magnetic elements is angularly offset relative to the alignment of the second set of displaced dipolar magnetic elements (b) moving in a reciprocal, rotational or orbital manner the magnetic device so that active agents in proximity to said device will be subject to alternating polarities of magnetic field and alternating magnetic gradients in response to said reciprocal, rotational or orbital movement.

Without being bound by any particular theory, it is believed that in general, increasing the magnetic flux beyond a certain limit does not lead to a continued increase in diamagnetic enhanced flow of active ingredient molecules. Instead, above a certain level the increased magnetic flux instead leads to increased thermal noise and or other disordering processes that act contrary to diamagnetic repulsion induced diffusion enhancement. This thermal noise causes an increase in the random movement of molecules that can overwhelm the diamagnetic repulsion effect created by the presence of a magnetic field.

Furthermore, the effect of a traditional uniform magnetic or electro-magnetic field on the dielectric tissues of the skin or dermis results in ionic polarization across the entire magnetic flux gradient rather than across adjacent regions. Polarization over such large distances limits the potential for enhanced micro fluidic flow. However in the case of the present invention, the use of one or more pairs of displaced dipolar magnetic elements linked by a magnetic return creates dielectric polarisation in closely adjacent regions that act to enhance micro-fluidic flow.

The present inventors have now identified that the utility of a magnetic field in enhanced delivery of active agents in cosmetic and medicinal skin compositions can be increased not just by increasing the strength of an individual magnetic field, but also by taking advantage of the differences between the flux of two magnetic fields of alternative polarity and orientation. The present invention thus allows dielectric polarization to be used to increase the permeability of target tissues in conjunction with the use of diamagnetic repulsion to enhance diffusion of active agents across barriers in such a manner that one effect does not negative the benefit of the other.

The inventors of the present invention believe that increasing the utility of the magnetic flux in this manner has a number of advantageous effects. It is known that increasing the magnetic flux increases the diamagnetic repulsion of the active agent away from the magnetic source and towards the target dermal barrier. This is a feature of diamagnetic susceptibility and is related to the paired electrons of diamagnetic molecules being repelled by magnetic fields. In this way, diamagnetic repulsion provides a means of adding directionality and mobility to molecules during diffusion.

The inventors further believe that that dielectric polarization of ionic species in target barriers could act to enhance penetration of active agents through induced osmotic and ionic effects. The inventors also believe that the increased flux, particularly perpendicular magnetic flux between two opposite poles, temporarily modifies or alters the barrier function and permeability, changing the microfluidic flow without permanently changing the physical structure of the surface.

However, the inventors of the present invention also believe that the diamagnetic repulsive effects of traditional uniform magnetic and electromagnetic fields tend to act contrary to the dielectric polarisation and therefore tend to cancel any benefit.

The inventors of the present invention thus believe that the present invention, comprising various arrangements of displaced dipolar magnetic pairs, allows diamagnetic repulsion to be maintained in the presence of dielectric polarization, thus providing an effective means of influencing molecular movement and permeation enhancements of barriers during the delivery of active agents.

This can be achieved by:

(a) juxtaposing two or more magnetic fields generated by one or more pairs of displaced dipolar magnetic elements linked by a magnetic return to achieve a spatially varying gradient of magnetic flux;

(b) moving two or more magnetic fields generated by one or more pairs of displaced dipolar magnetic elements linked by a magnetic return over a fixed point to achieve a temporally varying gradient of magnetic flux, or (c) a combination of (a) and (b).

Each pair of displaced dipolar magnetic elements of the present invention may, for the purposes of visualisation, be thought of in terms of a single traditional rod dipolar magnetic that is cleaved or broken around its central point and the two resulting sections rotated through 180° and brought together such that the opposite poles are adjacent (see, for example, FIG. 1). The magnetic return is used to integrate the magnetic fields at the point of cleavage. The result is a dipolar pair, displaced horizontally so as to provide both a perpendicular and a horizontal magnetic flux gradient.

In each pair of displaced dipolar magnetic elements, each individual dipole provides diamagnetic repulsion to the active agents which are to be transported across the dermal barrier, whilst the horizontal flux between each dipole pair acts to polarize the dielectric properties of the target tissue, inducing permeation changes.

The device of the present invention may comprise one pair of displaced dipolar magnetic elements, or may preferably comprise a number of pairs of displaced dipolar magnetic elements. For example, FIG. 1 shows a variety of arrangements of dipole pairs, arranged in rows or grids. The terms "pair" and "pairs" are used variously in the present specification, and reference to a single pair of displaced dipolar magnetic elements may be taken to also refer to multiple pairs of displaced dipolar magnetic elements.

The polarity of one pair of displaced dipolar magnetic elements may be in the same orientation as that of the neighbouring pair of displaced dipolar magnetic elements (i.e. the series may comprise [NS][NS][NS]) or may be in the opposite orientation (i.e. the series may comprise [NS][SN][NS]) (see FIG. 1).

There is also provided by the present invention use of a magnetic device for the delivery of a skin care active agent(s) comprising:

(a) applying an active agent(s) between a target dermal barrier and a magnetic device comprising one or more pairs of displaced dipolar magnetic elements linked by a magnetic return wherein the magnetic return is orientated on the surfaces of the dipole pair distal to the dermal barrier.

There is further provided use of a magnetic device for the delivery of a skin care active agent(s) comprising:

(a) applying an active agent(s) between a target dermal barrier and a magnetic device comprising one or more pairs of displaced dipolar magnetic elements linked by a magnetic return wherein the magnetic return is orientated on the surfaces of the dipole pair distal to the dermal barrier; and (b) moving in a reciprocal, rotational or orbital manner the magnetic device so that active agents in proximity to said device will be subject to alternating polarities of magnetic flux in response to said reciprocal, rotational or orbital movement.

In addition, there is provided use of a magnetic device for the delivery of a skin care active agent(s) comprising:

(a) applying a active agent(s) between a target dermal barrier and a magnetic device comprising at least two sets of pairs of displaced dipolar magnetic elements linked by a magnetic return wherein the magnetic return is orientated on the surfaces of the dipole pair distal to the dermal barrier and wherein the alignment of the first set of displaced dipolar magnetic elements is angularly offset relative to the alignment of the second set of displaced dipolar magnetic elements.

Finally, there is provided use of a magnetic device for the delivery of a skin care active agent(s) comprising:

(a) applying a active agent(s) between a target dermal barrier and a magnetic device comprising at least two sets of pairs of displaced dipolar magnetic elements linked by a magnetic return wherein the magnetic return is orientated on the surfaces of the dipole pair distal to the dermal barrier and wherein the alignment of the first set of displaced dipolar magnetic elements is angularly offset relative to the alignment of the second set of displaced dipolar magnetic elements (b) moving in a reciprocal, rotational or orbital manner the magnetic device so that active agents in proximity to said device will be subject to alternating polarities of magnetic field and alternating magnetic gradients in response to said reciprocal, rotational or orbital movement.

Preferably the uses provided above allow the improved and increased penetration of the active agents into the dermal barrier. Most preferably, such improved and increased penetration of the active agents leads to improved action of the active agent(s), which in turn leads to improved cosmetic or medicinal outcomes. For example, use of the present invention to increase the penetration of anti-acne agents such as salicylic acid into skin and follicles may lead to a reduction in the incidence of acne and improved healing of already present acne, or use of the invention to increase the penetration of moisturising agents into skin may increase the moisture content of the skin, lead to a reduction in the number of times such moisturising agents need be applied (thus providing cost benefits) and provide better and deeper penetration of the moisturising agents.

A magnetic return according to the present invention is a member that is adjacent to one surface of each of the members of the dipolar pair, passing from the positive polar surface of one of the pair of displaced dipolar magnetic elements to the negative polar surface of the other member of the pair of displaced dipolar magnetic elements wherein the magnetic return integrates the magnetic fields on those surfaces and reduces or eliminates the magnetic flux on those surfaces. The magnetic return may extend further to unite one set of dipole pairs with another set of dipole pairs, or a larger group of dipole pairs. The magnetic return is preferably located on the surfaces of the dipole pair distal to the biological dermal surface to which the magnetic fields are desired to be applied.

The magnetic return can be composed of any material that is magnetically conductive. Preferably, the material is a ferromagnetic material such as an iron compound (e.g. a ferrite such as barium ferrite, magnetite, or mild steel), a cobalt material, a strontium material, a barium material or a nickel material. The material may have a metalloid component such as boron, carbon, silicon, phosphorus or aluminium. Rare earth material such as neodymium or samarium may also be used.

The magnetic return preferably links the pair of displaced dipolar magnetic elements by covering all or at least some of one polar surface of the first magnet of the pair, and all or at least some of the opposite polar surface of the second magnet of the pair.

The device may also comprise a housing for the pairs of displaced dipolar magnetic elements. Preferably, the housing does not interfere with the generated magnetic fields.

The movement described herein may be either through manual operation or through mechanical means. Where the movement is delivered through manual operation (ie through normal consumer actions such as brushing or scrubbing) is used to mobilize the magnetic device the frequency will be in the order of 1 Hz to 5 Hz. In such cases, the strength of the magnet field produced by each element of the magnet array should be between about 100 and 500 Gauss. In the alternate, where movement is delivered through mechanical or electrical means (such as in the form of a electrical brush like an electrical tooth brush) the oscillation should be in the order of approximately 100 and 8,000 Hz with a magnet flux of between about 100 and 1000 Gauss.

As used herein, rotational includes movement in an arc-like, semi-circular, circular or orbital manner.

In a particular form of the invention the magnetic device includes a means for moving the magnetic device over the dermal barrier. Such a means will include any mechanism, electronic or mechanical, adapted for reciprocal or rotational movement of the magnetic material. For example, the magnetic material may be associated with a drive mechanism that is capable of reciprocal movement.

According to the invention, magnetic materials include, without limitation:

a. arrangements where individual segments or sections of magnetized ferromagnetic materials are assembled in the configuration described herein; and b. arrangements where magnetic particles or elements are disposed in a solid or semi-solid matrix or base and the required magnetic pattern is impressed upon the ferromagnetic particles.

The present invention may be constructed using a range of magnetic materials exhibiting ferromagnetic properties. Such materials may include Iron, Strontium, Barium, Cobalt or Nickel with a metalloid component such as Boron, Carbon, Silicon, Phosphorus or Aluminium. Alternately, rare-earth materials such as Neodymium or Samarium-cobalt may also be used. Such ferromagnetic materials may be deployed as rigid elements within a device or encapsulated in a flexible matrix such as rubber or silicone.

Generally, each pair of displaced dipolar magnetic elements of the present invention has a horizontal offset between centres of between 1 and 10 millimeters, preferably 3 and 7 millimeters. As a result, pairs of displaced dipolar magnetic elements may be disposed at a repetition rate of between 2 and 10 dipolar pairs per centimeter, more preferably 1.5 and 4 dipolar pairs per centimeter.

Preferably, the poles in a particular spatial region are between 1.0 mm to 10 mm apart, more preferably, the poles are between 1.0 mm to 5.0 mm apart.

In another aspect of the invention, the magnetic flux of each magnetic pole is between about 10 Gauss and about 1000 Gauss. Preferably, the flux of each pole is between about 100 Gauss to about 600 Gauss, most preferably about 125 to 450 Gauss.

In another aspect, the difference or delta flux between the magnetic flux of two adjacent poles of opposite polarity is between about 100 Gauss and about 2000 Gauss. More preferably, the difference between the magnetic flux of two adjacent poles of opposite polarity is between about 200 Gauss to about 1400 Gauss, most preferably about 200 to 900 Gauss.

Figure 2A:
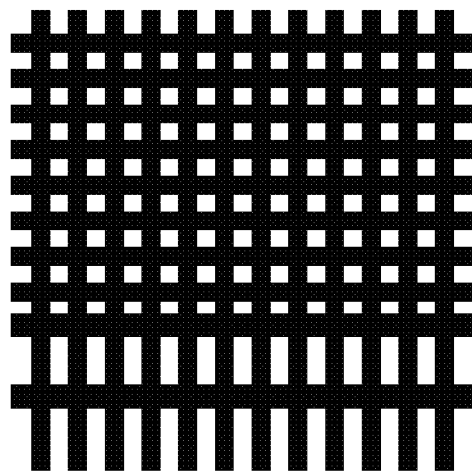
FIGS. 2A-2C provide an example of a device according to the present invention which consists of two sets of displaced dipolar magnetic elements wherein the orientation of the second set is 90° to the orientation of the first set.
Figure 2B:
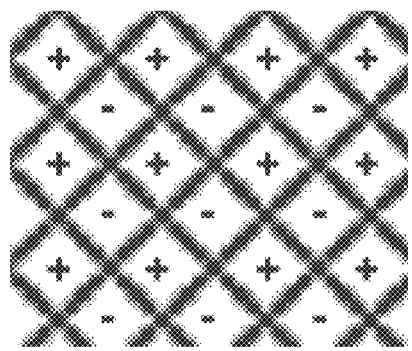
Figure 2C:
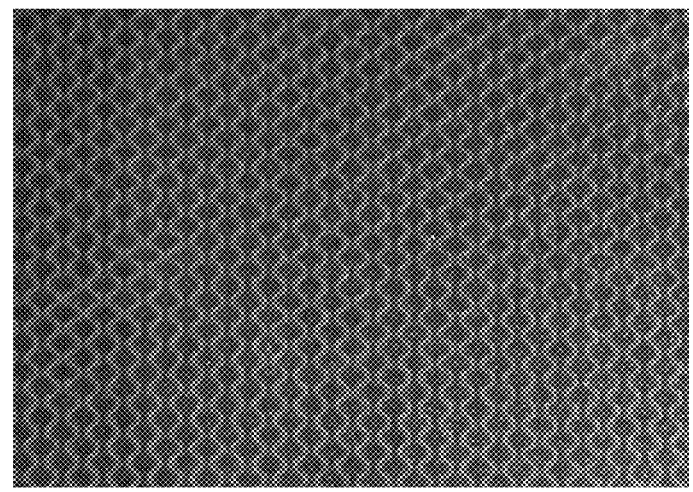
Figure 3A:
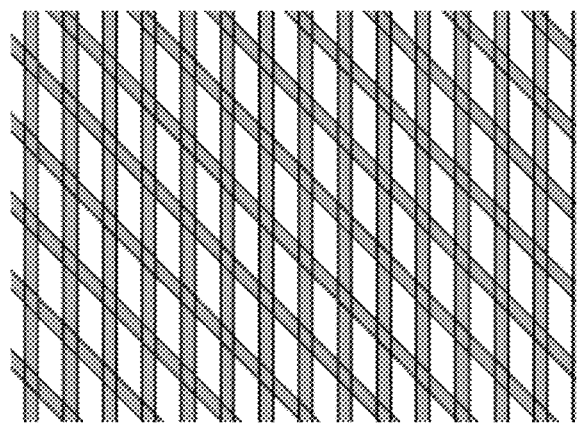
FIGS. 3A-3C provide an example of a device according to the present invention which consists of two sets of displaced dipolar magnetic elements wherein the orientation of the second set is 45° to the orientation of the first set.
Figure 3B:
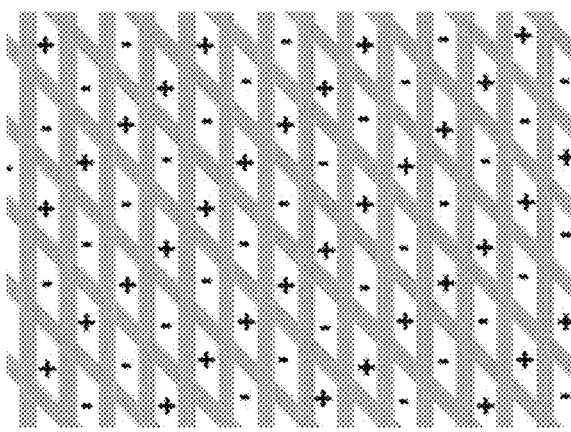
Figure 3C:
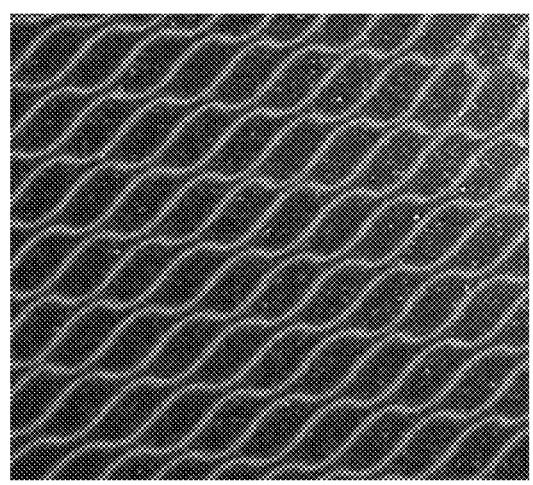
Figure 4:
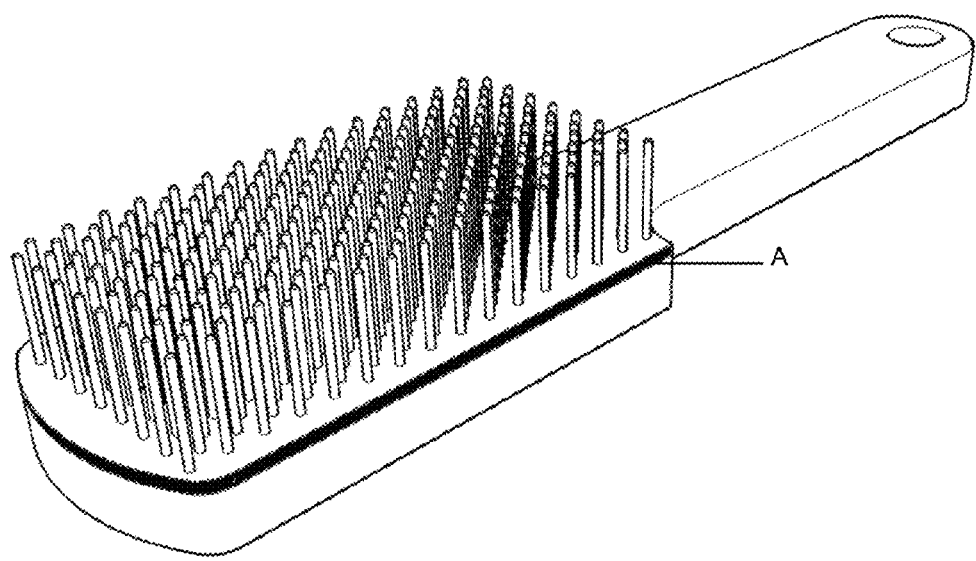
FIG. 4 is an example of a brush comprising the device of the invention, wherein the pairs of displaced dipolar magnetic elements are provided in a sheet-like arrangement within the head of the brush (A).
Figure 5:
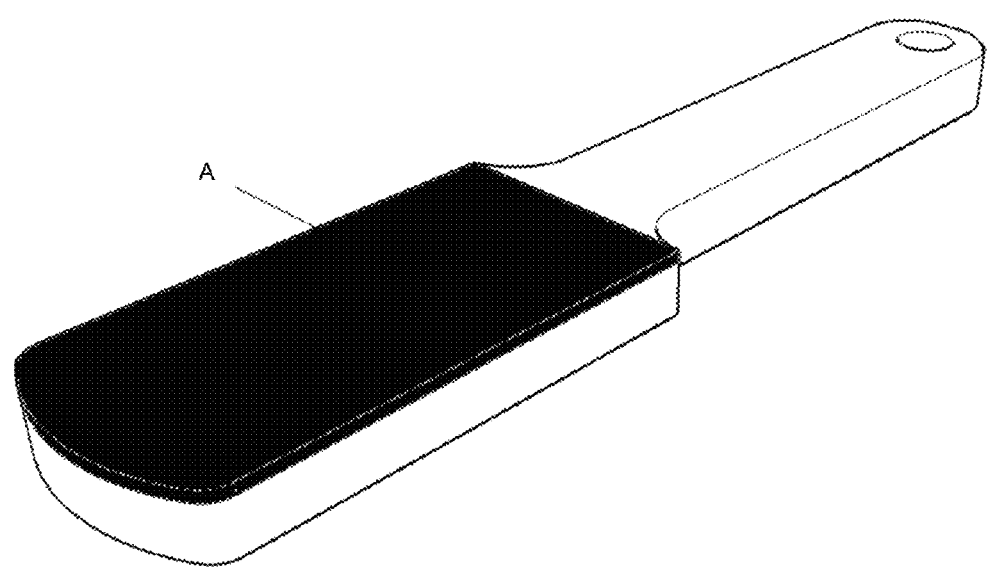
FIG. 5 is an example of a brush comprising the device of the present invention, wherein the pairs of displaced dipolar magnetic elements are in the form of a sheet (A), wherein the brush is moved over the dermal barrier without the need for bristles.
Figure 6:
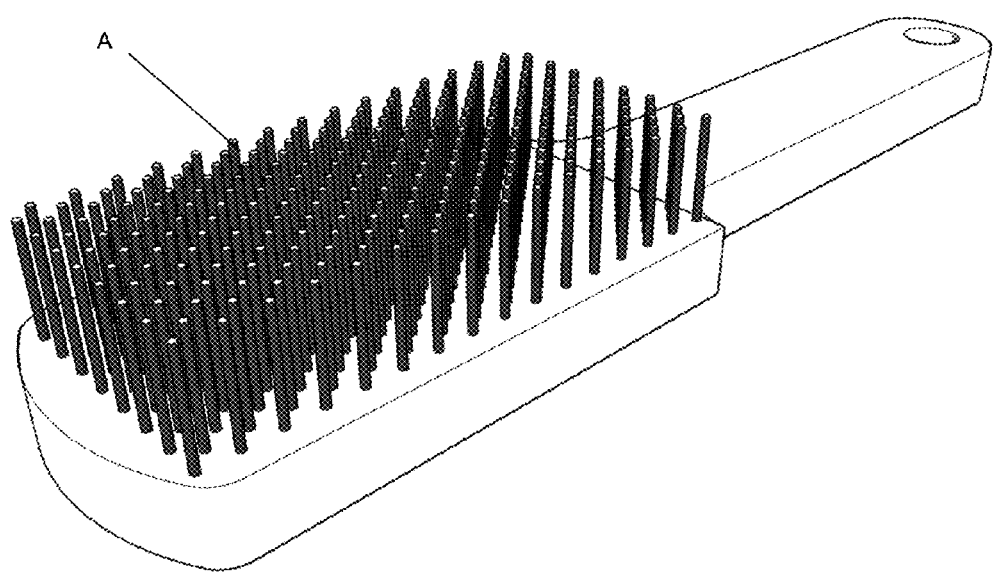
FIG. 6 is an example of a brush comprising the device of the invention, wherein the pairs of displaced dipolar magnetic elements are laminated to a handle body such that they replace the role of bristles (A).
Figure 7:
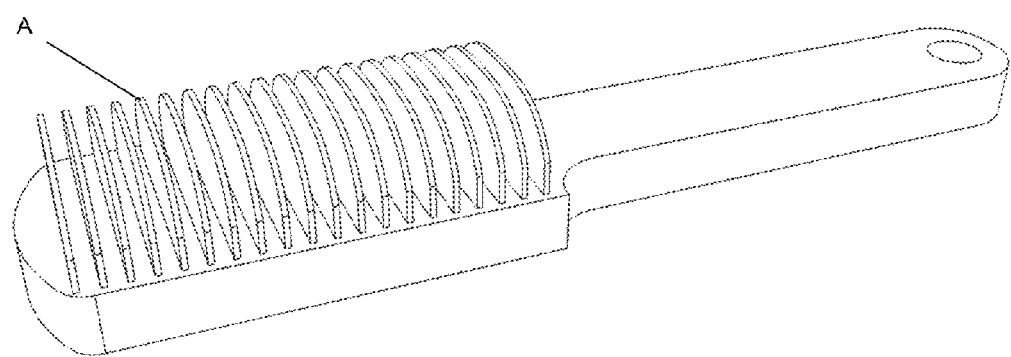
FIG. 7 is an example of a brush comprising the device of the invention, wherein the traditional monofilament bristles of the brush have been replaced with panels of pairs of displaced dipolar magnetic elements (A) in accordance with the present invention.
Figure 8:
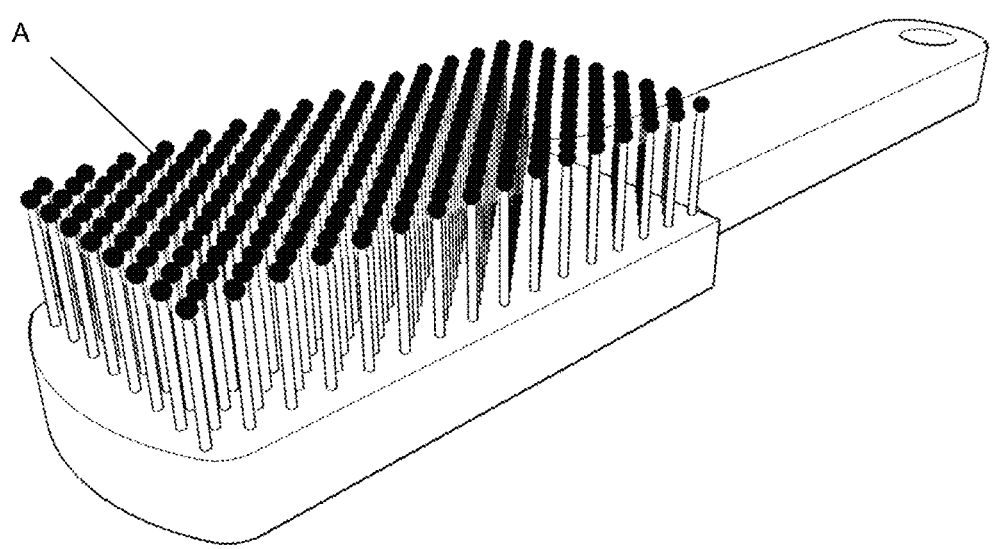
FIG. 8 is an example of a brush comprising the device of the invention, wherein the bristles of the brush have been capped or terminated pairs of displaced dipolar magnetic elements in the form of balls or domes (A).
Figure 9:
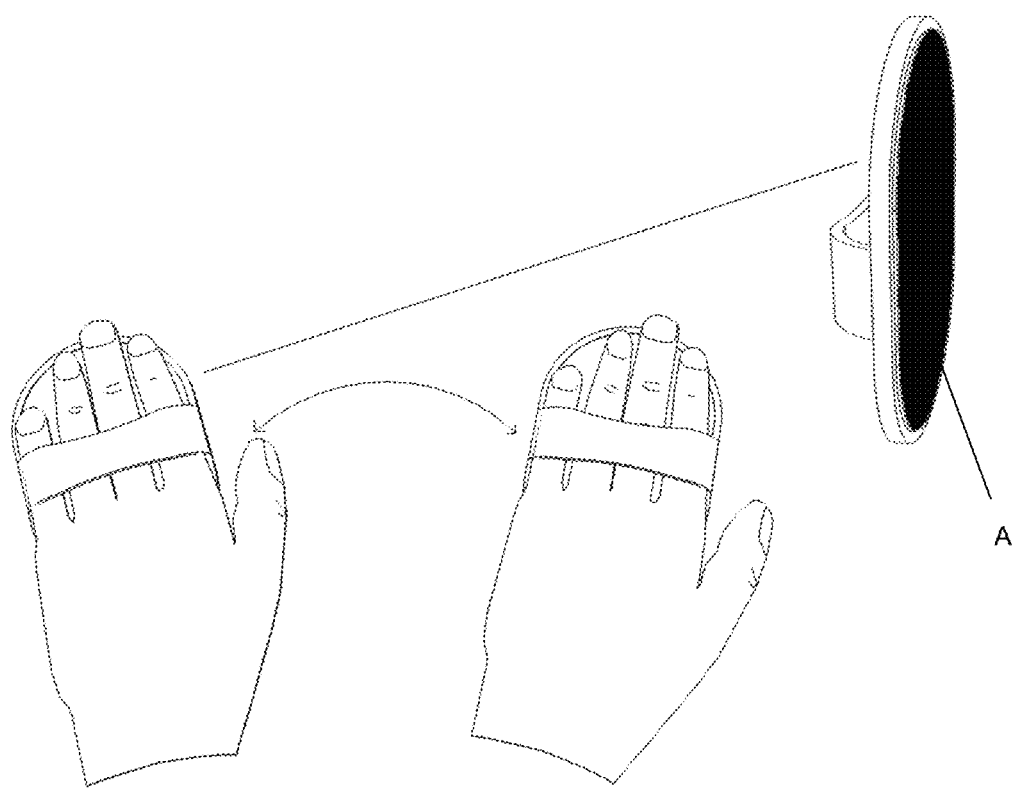
FIG. 9 is an example of a pad comprising a sheet of pairs of displaced dipolar magnetic elements (A) which is further provided with a flexible or rigid backing panel and a handle.
Figure 10:
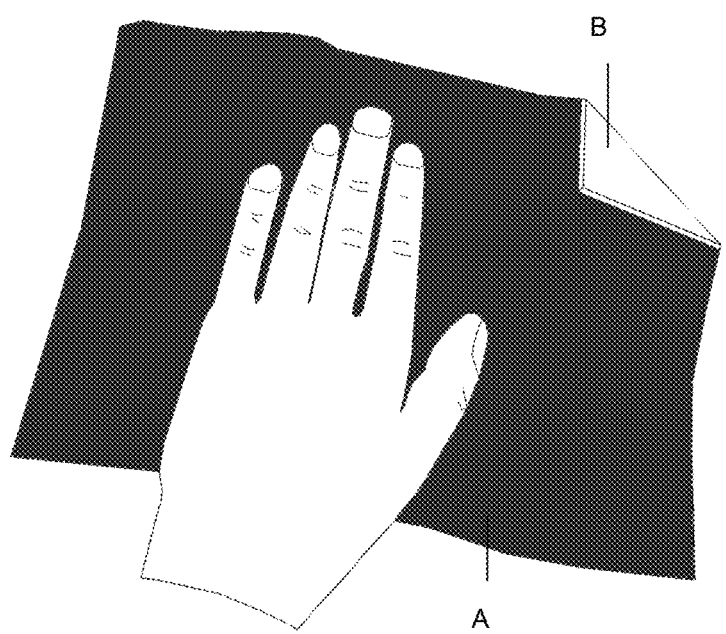
FIG. 10 is an example of a flexible membrane (A), such as a plastic film or woven piece of fabric, wherein they are provided as a sheet adhered to one side of the membrane (B). Alternatively, the membrane may comprise a flexible matrix within which the pairs of displaced dipolar magnetic elements are distributed.

When the magnetic device comprises at least two sets of pairs of displaced dipolar magnetic elements wherein the alignment of the first set of displaced dipolar magnetic elements is angularly offset relative to the alignment of the second set of displaced dipolar magnetic elements, the orientation of the first set of dipolar pairs is preferably between about 1° and 90° relative to the second set of dipole pairs. Preferably, the degree of angular offset is at least 10°, more preferably at least 45°, most preferably between about 45° and 90°. FIGS. 2 and 3 provide examples of arrangements of sets of pairs of displaced dipolar magnetic elements.

Such magnetic devices with at least two sets of pairs of displaced magnetic elements may have a different number of dipolar pairs disposed in the first set from that in the second set. For example, the first set of dipolar pairs may have two dipolar pairs per centimeter whilst the second set may have five dipolar pairs per centimeter.

Where a different number of dipolar pairs is used in each set of dipolar pairs in differing orientations, the magnetic fields will be complex and exhibit different flux densities in each orientation, as the fields produced by the first set of dipolar pairs will sum with that of the second set of dipolar pairs at the points of constructive and destructive interference and by doing so provide a net field of higher magnetic strength, higher magnet flux and higher magnetic gradient, all of which will add to the utility of the present invention.

The purpose of multiple intersection orientations is two-fold:
  (i) To accommodate non-linear movements either by users or by devices. Then induction effect is reliant on the target barrier being influenced by an alternating field, which only happens when the device is tracked across the barrier at 90° to the alignment of the elements. To accommodate a circular motion, the arrays are aligned so to produce an AC like induction, irrespective of the direction of motion; and
  (ii) To induce opposing charges in adjacent areas of the barrier so to produce streaming potentials to accommodate pathways that are not perpendicular to the field flux, such as vertical shunts or pathways.

The device may further comprise more than two sets of dipolar pairs. The orientation of these further sets of pairs of displaced dipolar magnetic elements may align with the first set of pairs of displaced dipolar magnetic elements and thus be angularly offset to the second set of pairs of displaced dipolar magnetic elements, or may align with the second set and thus be angularly offset to the first set of pairs of displaced dipolar magnetic elements. Further orientations and arrangements of sets of pairs of displaced dipolar magnetic elements may be provided which align with either the first or second sets of displaced dipolar magnetic elements. For example, a many layered device may be provided which comprises a number of orientation of pairs of displaced dipolar magnetic elements stacked on top of each other, each one aligned in a different orientation to the array below (e.g. each set aligned perpendicular to the set below).

In one embodiment of this invention the target surface is a skin dermal barrier, such as, for example the layers of the skin (epidermis, dermis), including the stratum corneum, granular cell layer, spinous cell layer, basal cell layer, and other components of the integumentary system and the like. In this form of the invention the device is preferentially adapted to deliver active agent(s) across the dermal and other integumentary barriers. Such dermal and integumentary barriers may have micro channels, apertures, pores etc through which active agents can be delivered.

According to a form of the invention the method of the invention provides a means for driving the passage of active agent(s) across the barrier formed by a target dermal or integumentary barrier such as the epidermis, dermis, stratum corneum, follicles, pores etc into a subject (including a patient). The method may be enhanced by the additional step of pairing the device with an alternate drug delivery system that operates either in conjunction with, or in parallel with, the device, to promote the passage of active agents through the dermal barrier. Such alternate drug delivery systems may include, for example, iontophoresis, drug-adhesive matrix, chemical penetration enhancers, micro-needles and sonophoresis.

The process of enhanced delivery by the present invention involves the utilization of magnetic principles to apply force upon active agent(s) in such a manner as to ensure that the force acting upon the agents is different from that acting upon the molecules of the vehicle, gel or solvent. As a result, another method of improving the utility of the invention is to select or chemically alter the diamagnetic sensitivity of the active agent or that of the vehicle, gel or solvent in which it is located with the view to enhancing the differences in diamagnetic sensitivity between the two entities. By way of example, the additional of a light ester such as phenxyethyl acrylate to a diethylaminoethyl acrylate polymer may act to increase the diamagnetic susceptibility of the polymer and by doing so increase the delivery of a diamagnetic target molecule from that vehicle, gel or solvent.

According to a particular form of the invention, the device is in the form of an adhesive dressing, comprising a plurality of displaced dipolar magnetic pairs in planar sheet format with an active ingredient entrapped or dissolved in a drug-in-adhesive matrix. The device as disclosed may adhere to the skin. In such form, the plurality of displaced dipolar magnetic pairs will act upon the active ingredient enhancing diffusion form the drug in adhesive matrix and enhanced delivery and bioavailability at a skin barrier whose permeability has been alter by the magnetic effects of displaced dipolar magnetic pairs.

In another a form of the invention the device is formed as a brush, with the active agent located on some or all of the bristles of the brush or applied separately to the dermal barrier to be brushed.

If the device of the invention is in the form of a brush, then the displaced dipolar magnetic pairs may be used as a form of the body, as a component of the bristles or as a form of the body in which the magnetic effect is transmitted through the bristles by nature of their magnetic conductivity. In such cases the active agent can enter the dermal barrier when the bristles are contacted with the dermal barrier or in response to the effects of displaced dipolar magnetic pairs remotely located but whose effect is transmitted by said bristles. In a desirable form, the device of the invention is provided in the form of a manual or electrically operate brush device (somewhat like a toothbrush), with the magnetic materials located in the head of the brush near the base of the bristles and the active agent being located on the bristles of the brush device.

As the brush is moved over the skin surface, the moving magnetic field enhances the ability of the active agent to penetrate the dermal barrier.

In another a form of the invention, the device comprises a pad within which is located a flexible or inflexible magnetic material. The pad may be reversibly applied or adhered to the dermal barrier to which the active agents is desired to be delivered. Alternatively, the patch- or pad-like device may be rubbed over the dermal barrier. If movement is used, the movement of the pad comprising the magnetic component enhances the penetration of the active agents in accordance with the method of the present invention.

The active agent may be releasably contained within the pad, with the active agent(s) present within the pad, permeating the pad and being capable of diffusing out of the pad and penetrating the dermal barrier. Alternatively, the active agents may be applied to the dermal barrier prior to application or adhering of the pad to the dermal barrier or prior to rubbing of the pad over the dermal barrier.

In another form of the invention, the device may comprise a roller applicator or pen device which can be moved or rubbed over the dermal barrier. The active agent may be applied to the device prior to it being rubbed over the dermal skin surface, or the active agent may be applied to the surface prior to the device being rubbed or moved over it.

In a further form of the invention, the device may include a polymer coating comprising a backing layer that is substantially impermeable to active substances located adjacent the magnetic material.

The active agent(s) delivered by the device of the invention may cover the entire region of the contact zone between the device and the skin or alternatively may be formed in islands therein. In a preferred form, the active agent(s) are located between the inventive device and a subject's dermal barrier.

Suitable active agent(s) that can be delivered by the invention include any active agent(s) exhibiting negative magnetic susceptibility and any active agent(s) having therapeutic, cosmetic, restorative, antimicrobial, anti-fungal, cleaning or disinfectant beneficial properties when administered to a surface as described herein. When the invention is employed to assist in the passage of active agents across a biological barrier such as such as skin the class of active agents, include, for example, proteins, peptides, nucleotides, anti-obesity drugs, corticosteroids, analgesics, anti-fungal agents, oncology therapies, cardiovascular agents, anti-inflammatory agents, non-steroidal anti-inflammatory agents, anti-arrhythmic agents, antibiotics, anticoagulants, antidepressants, antidiabetic agents, antiepileptics, antihistamines, anti-hypertension agents, anti-neoplastic agents, immunosuppressants, anti-thyroid agents, antiviral agents, sedatives, astringents, beta-adrenoceptor blocking agents, diuretics, muscle reactants, prostaglandins, sex hormones, anti-allergic agents, stimulants, vasodilators, xanthenes, antioxidants, vitamins, nutrients, skin restorative agents, hair care or restorative agents and those active agents delivered as nutraceuticals, cosmeceutical or cosmetics to or through a biological barrier such as skin.

Non-limiting examples of pharmaceutical and biopharmaceutical active agents which could be delivered using the method of the present invention to the skin include:

a) steroids such as sulfonamides, triamcinolone, betamethasone, budesonide, cortisone, dexamethasone, hydrocortisone, methylprednisolone, prednisolone, prednisone sodium phosphate, fluorometholone, rimexolone, medrysone alcohol, 11-desoxcortisol, and anecortave acetate and the like b) anti-inflammatory agents such as hormonal agents, clobetasol, dexamethasone, acetyl salicylic acid, glycyrrhizic acid or glycyrrhetic acid, hydrocortisone, prednisolone, prednisone, non-hormonal agents, allopurinol, aspirin, indomethacin, phenylbutazone and the like;

c) antibiotics such as the cephalosporins, chloranphenical, gentamicin, Kanamycin A, Kanamycin B, the penicillins, ampicillin, streptomycin A, antimycin A, chloropamtheniol, metromidazole, oxytetracycline penicillin G, the tetacyclines and the like;

d) anti-acne agents, such as salicylic acid and benzoyl peroxide;

e) antimicrobial or antifungal agents such as, for example, caprylyl glycol, triclosan, phenoxyethanol, erythromycin, tolnaftate, nystatin or clortrimazole;

f) chelating agents, such as EDTA and the like;

g) topical analgesics, such as benzocaine, tetracaine, lidocaine or procaine and the like;

h) peptides with either therapeutic benefit or cosmetic benefit comprising between two and 20 amino acid residues, preferably, between three and 10 amino acid residues (cosmetic peptides such as palmitoyl pentapeptide or argireline which have beneficial effect on skin cells eg whitening, free-radical scavenging, anti-aging, stimulation of collagen synthesis, moisturizing, antimicrobial, anti-inflammatory, or anti-irritant) and the like.

Non-limiting examples of neutraceutical active agents which could be delivered using the method of the present invention to the skin include:

a) Vitamins and nutrients including essential amino acids and the like;

b) Electrolyte replacements such as potassium chloride and the like;

c) Antioxidants or free-radical scavengers: such as ascorbic acid, its fatty esters and phosphates, tocopherol and its derivatives, N-acetyl cysteine, sorbic acid and lipoic acid and the like;

Non-limiting examples of cosmetic active agents which could be delivered using the method of the present invention to the skin include:

a) Moisturising agents and emollients: occlusive agents e.g. hydrocarbons such as petrolatum, silicone containing agents such as dimethicone, cyclomethicone, fatty acids and alcohols such as lanolin acid or alcohol, sterols such as cholesterol, waxes and fats such as cocoa butter, carnuba wax and bees wax; humectants e.g. glycosamines such as hyaluronic acid, glycerine, honey, urea, lactic acid, α-hydroxy acids, propylene glycol etc;

b) Anti-aging compounds: such as retinoids or hydroxy acids;

c) Deodorants: including alcohol based deodorants; deodorants containing antimicrobial agents such as triclosan or metal chelating agents; perfumes and essential oils;

d) Antiperspirants: including aluminium based compounds such as aluminium chloride, aluminium chlorohydrate, and aluminium-zirconium compounds (aluminium zirconium tetrachlorohydrex gly and aluminium zirconium trichlorohydrex gly); potassium alum and ammonium alum;

e) Fragrances: such as essential oils, musk, alcohols (eg furaneol, menthol), esters (eg fructone, ethyl methylphenylglycidate), ketones (eg dihydrojasmone), lactones (eg coconut odour, jasmine lactone);

f) Astringents: such as clove oil, menthol, camphor, eucalyptus oil, eugenol, menthyl lactate, witch hazel distillate, aluminium based compounds and the like;
g) Skin lightening agents: such as liquorice, ascorbyl phosphates, hydroquinone or kojic acid and the like;
h) Sun protecting agents (organic or inorganic): such as avobenzone, oxybenzone, octylmethoxycinnamate, titanium dioxide or zinc oxide;
i) Exfoliating agents (chemical or physical): such as N-acetyl glucosamine, mannose phosphate, hydroxy acids, lactobionic acid, peach kernels, or sea salts and the like;
j) Self-tanning agents: such as dihydroxyacetone;
k) Colouring agents for skin and mucosal surfaces;
l) Plumping agents and fillers: such as hyaluronic acid or hyaluronate.
m) Other agents such as aloe vera.

Additional agents that could be delivered to the skin surfaces include additional nutritional type ingredients, such as vitamins, minerals, amino acids, vitamin E, and folic acid; sensate ingredients, such as those providing cooling (such as menthol), tingle, or heat sensations (such as capsaicin or capsicum oil); colorants or other aesthetic agents; and combinations thereof. Essential oils may also be delivered by the present invention, such as oils of lavender, rose, rosemary, spearmint, peppermint, wintergreen, eucalyptus, lemon, lime, grapefruit, and orange.

The above list of active agent(s) may be applied in a controlled manner, using the method of the present invention. This list is not exhaustive. Preferably, any active agent(s) that can be delivered systemically or topically can potentially be delivered using the present invention.

The active agent may be in the form of a gel, paste, liquid, thermo-reversible gel or paste, etc. For example, the active agent(s) may be in the form of moisturising creams, medicinal ointments or skin refreshing sprays/spritzes.

While the active agent(s) may be provided and used alone with the device, in many situations the active agent will be included in a formulation either alone or in combination with one or more other active agents. Where the formulation is to provide a pharmaceutical and/or biopharmaceutical benefit, the number of active agent(s) included in the formulation may preferentially be quite selective. Where the formulation provides a nutraceuticals, cosmetic and/or cosmeceutical effect, the number of active agents may be much greater in number.

The formulation employed in the delivery process may include additives such as other buffers, diluents, carriers, adjuvants or excipients. Any pharmacologically acceptable buffer that is magnetically inert or neutral or which has a magnetic susceptibility that is either paramagnetic in nature or greater than that of the active agent(s) being delivered, may be used, e.g., tris or phosphate buffers. Other agents may be employed in the formulation for a variety of purposes. For example, buffering agents, preservatives, co-solvents, surfactants, oils, humectants, emollients, chelating agents, stabilizers or antioxidants may be employed. Water soluble preservatives which may be employed include, but are not limited to, benzalkonium chloride, chlorobutanol, thimerosal, sodium bisulfate, phenylmercuric acetate, phenylmercuric nitrate, ethyl alcohol, methylparaben, polyvinyl alcohol, benzyl alcohol and phenylethyl alcohol. A surfactant may be Tween 80. Other vehicles that may be used include, but are not limited to, polyvinyl alcohol, povidone, hydroxypropyl methyl cellulose, poloxamers, carboxymethyl cellulose, hydroxyethyl cellulose, purified water, etc. Tonicity adjustors may be included, for example, sodium chloride, potassium chloride, mannitol, glycerin, etc. Antioxidants include, but are not limited to, sodium metabisulfite, sodium thiosulfate, acetylcysteine, butylated hydroxyanisole, butylated hydroxytoluene, etc.

The indications, effective doses, contra-indications, vendors etc, of the active agents in the formulations are available or are known to one skilled in the art.

The active agents may be present in individual amounts of from about 0.001 to about 5% by weight and preferably about 0.01% to about 2% by weight. However, it is contemplated that the active agents may be present in individual amounts greater than this, for example up to 100%.

Suitable water soluble buffering agents that may be employed include sodium carbonate, sodium borate, sodium phosphate, sodium acetate, sodium bicarbonate, etc., as approved by the US FDA for the desired route of administration. These agents may be present in amounts sufficient to maintain a pH of the system of between about 2 to about 9, preferably about 4 to about 8, more preferably 4.5, 5, 5.5, 6, 6.5, 7 or 7.5 (or any pH in between). As such the buffering agent may be as much as about 5% on a weight to weight basis of the total formulation. Electrolytes such as, but not limited to, sodium chloride and potassium chloride may also be included in the formulation where appropriate.

The active agents to be delivered using the device of the present invention may be provided in a matrix layer. If the active agent delivered by the device of the present invention is contained within a matrix, the matrix preferably allows the active agent to diffuse or exit the matrix in some manner and contact the dermal barrier, perhaps by moving down the bristles of the brush to the dermal barrier.

The matrix is preferentially prepared from a polymer or copolymer prepared from e.g., polyisobutylene, ester of polyvinyl alcohol, polyacrylic and polymethacrylic acid esters, natural rubber, polymers of styrene, isoprene, and styrene-butadiene or silicone polymers, resin components, such as, saturated and unsaturated hydrocarbon resins, derivatives of abietyl alcohol and of beta-pinene, plasticizers, such as phthalic acid esters, triglycerides and fatty acids, as well as a series of other substances known to those skilled in the art.

Matrix biocompatible polymers that might be used in the invention include compounds such as polycaprolactone, polyglycolic acid, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (SAIB), and other polymers such as those disclosed in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety.

The matrix containing the active agents may also be prepared from thermosetting polymers such as tetra-substituted ethylene diamine block copolymers of ethylene oxide and propylene oxide (e.g., poloxamine); polycarbophil; and polysaccharides such as gellan, carrageenan (e.g., kappa-carrageenan and iota-carrageenan), chitosan and alginate gums.

The matrix may also be a hydrogel, being a gel prepared with hydrophilic polymers, and these materials are well known in the art, frequently being used as part of biomedical electrodes, such as are described in U.S. Pat. Nos. 6,631,294 and 6,845,272, the contents of which are incorporated herein by reference. Examples of hydrophilic polymers useful for the preparation of hydrogels are polyacrylate, polymethacrylate, polyacrylamide, poly(vinyl alcohol), poly(ethylene oxide), poly(ethylene imine), carboxy-methylcellulose, methylcellulose, poly(acrylamide sulphonic acid), polyacrylonitrile, poly(vinyl-pyrrolidone), agar, dextran, dextrin, carrageenan, xanthan, and guar. The preferred hydrogels are acrylates and may be, for example, preferably made from acrylic esters of quaternary chlorides and/or sulfates or acrylic amides of quaternary chlorides; polymers of this type are disclosed in U.S. Pat. No. 5,800,685, incorporated herein by reference. The hydrophilic polymers will generally constitute from about 1 to about 70%, preferably about 5 to about 60%, more preferably about 10 to about 50%, by weight of the hydrogel.

In a highly preferred form of the invention, a topical formulation for delivery to a subject is prepared by selecting a desired amount of active agent. The agent is then preferably placed in a suitable delivery matrix. The amount of the active agent to be administered and the concentration of the compound in the topical formulation depends upon the diluent, delivery system or device selected, the clinical or cosmetic condition of the subject, the side effects and the stability of the active agent in the matrix.

Non-limiting Illustration of the Invention

Further features of the present invention are more fully described in the following non-limiting Examples. This description is included solely for the purposes of exemplifying the present invention. It should not be understood as a restriction on the broad description of the invention as set out above.

Example 1

Experiments involved the application of the humectant and moisturising compound Urea in the form of gel and occlusion to the volar forearm of healthy volunteers.

Each forearm was divided into three sites for application of the active agent, a 5% Urea gel (a cosmetic moisturising compound known to be taken up by the skin, resulting in a thickening of the epidermis). The central site was used for passive topical application of the urea. Urea was also applied to the sites either side of the central control site, with these locations being further exposed to 25 mm square sections comprised multiple pairs of displaced magnetic dipolar elements of 450 peak gauss field strength aligned linearly in parallel common pole format, forming lines of common pole fields spatially separated by 4 mm between paired centres.

Figure 11:
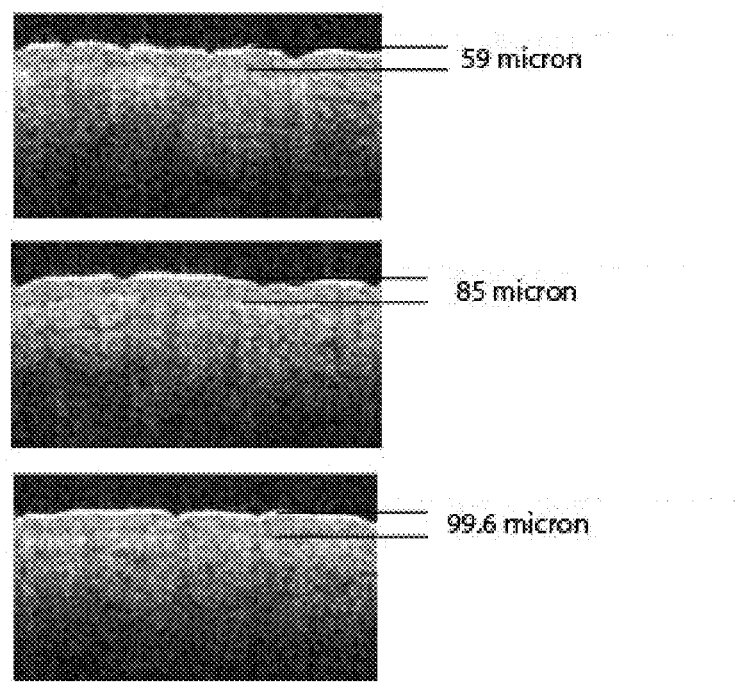
FIG. 11 represents measured changes in human epidermal thickness as recorded by Optical Coherence Tomography in response to the application of the humectant Urea for 20 minutes, comparing epidermal thickness changes. The images show base line thickness (top) or initial epidermal thickness, the change in thickness caused by normal passive transdermal delivery after 20 minutes of passive moisturing (centre) and the change in thickness caused by exposure of the epidermis to pairs of displaced dipolar magnetic elements after 20 minutes of active moisturing (bottom).

Urea was applied to all three sites for a period of 20 minutes. All study sites were occluded using Parafilm® secured using micropore breathable surgical tape to eliminate any potential occlusive effects. After 20 minutes, the sites were cleared of all materials and remaining gel and analysed by Optical Coherence Tomography (OCT) laser imaging to determine morphological changes. OCT is an imaging technique that uses laser light scattering to construct a detailed 3-D image of the sub-surface structures of living skin at a resolution similar to a standard microscope, allowing accurate monitoring of physical changed in skin morphology during and following the application of active ingredients. The results of these tests are provided in FIG. 11.

OCT data was analysed using three established and previously published optical techniques:

Total epidermal pixel count. This involved the manual selection of the region encompassed by the stratum corneum and dermal/epidermal boundary. This was then coloured using a primary fill and pixels calculated by histogram, so can be seen in FIG. 11.

Area selected pixel count. This involved the selection of a 200 by 150 pixel zone on each image free of surface and subsurface irregularities. The area of the stratum corneum and epidermis was then extracted using a pixel count technique.

Filter selected area pixel count. This involved the use of various grey-scale threshold filtering techniques to isolate pixels of a preset luminosity prior to counting.

Results show that standard topical application of urea in vivo caused epidermal hydration and results in an increase in epidermal thickness of approximately 26 microns or 40%. Urea, when delivered into the epidermis and exposed to the magnetic fields of the present invention increased epidermal thickness by over 40 microns or almost 70%.

Example 2

In a further in vivo experience, two examples of arrays comprising pairs of displaced magnetic dipolar elements of the present invention were studied to illustrate the essential requirement for the pairs of displaced magnetic dipolar elements to be correctly configured to the diamagnetic property of the active ingredient to be delivered, in addition to the dielectric properties of the target receptor barrier.

Figure 12:
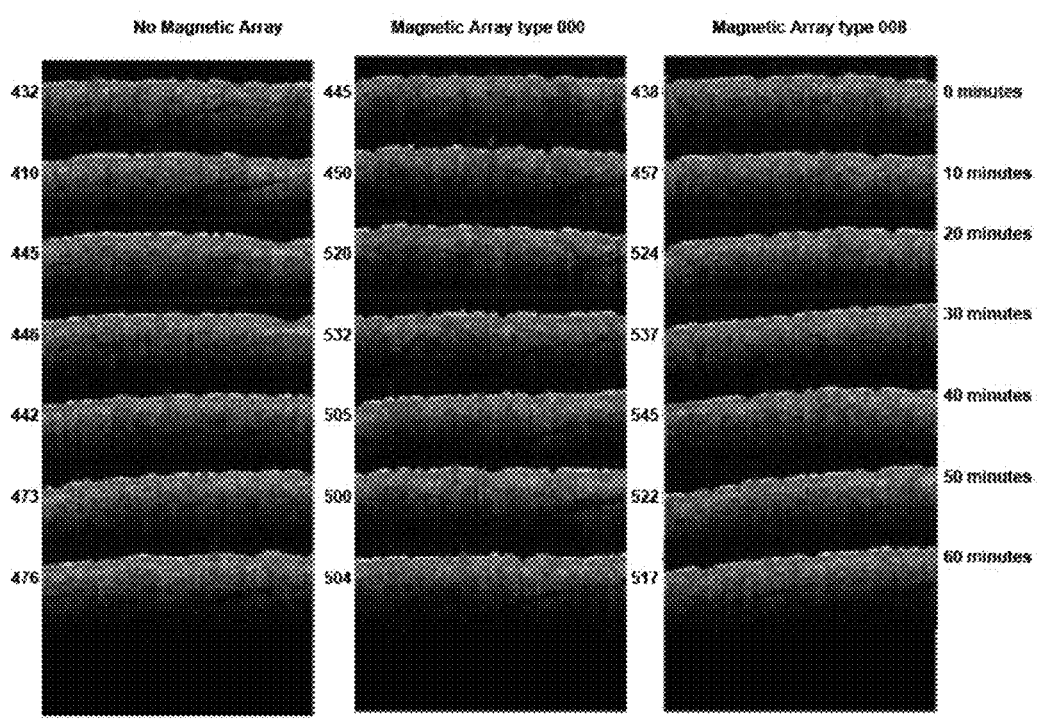
FIG. 12 is a series of images produced using Optical Coherence Tomography showing the time dependent change in epidermal thickness caused by the humectant Urea when delivered into the skin using two forms of the present magnetic array invention when compared with normal topical application.

Urea was applied to skin in a similar manner to Example 1. The urea and occlusive dressings were removed at 10 minute time periods to take measurements using OTC, with the urea and occlusive dressing being immediately replaced after each set of measurements. Each site was imaged in triplicate for each time point (i.e. three sites, triplicate images, seven time points). The laser images were then analysed to determine the differential change in skin morphology in response to the penetration of urea into facial skin under the influence of two different configurations of the present invention. FIG. 12 summaries this experiment, with the thickness of the epidermis provided next to the image.

Magnetic array Type ETP000 is a magnetic array in which a parallel linear array of common pole pairs of 250 gauss peak flux with a centre to centre spatial separation of 2 mm. Magnetic array Type ETP008 is a parallel linear array of common pole pairs of 450 gauss peak flux with a centre to centre spatial separation of 4 mm.

Results show that passive regions experienced an increase in epidermal thickness of 103.2% at 30 minutes and 110% after 60 minutes of Urea penetration.

Magnetic array Type ETP000 showed a more rapid epidermal thickness change of 119.5% at 30 minutes and 113.25% at 60 minutes.

Magnetic Array Type ETP008 showed a less rapid initial epidermal thickness change of 112.6% at 30 minutes but a more sustained enhancements of 118% at 60 minutes.

The different arrangements of the pairs of displaced magnetic dipolar elements provided different penetrative enhancement of the active agents. Such differences illustrate the complex relationships between diamagnetic characteristics of the target ingredient being delivered and the design and format of the pairs of displaced dipolar elements that embody the present invention.

Example 3

As a further example, an additional experiment was undertaken to explore the time dependent changes in measured epidermal thickness using four different configurations of the present invention when compared to passive application.

As in previous examples, all test areas of skin were treated using a 5% Urea gel formation and occluded with Parafilm. The urea and occlusive dressings were removed at 30 minutes and 60 minutes to allow measurements to be taken, with the urea and dressing being immediately replaced after the 30 minute test. Four different arrangements of the pairs of displaced magnetic dipolar elements present invention were studied to elucidate the complex relationship between enhanced delivery to human skin and the specific arrangements of the pairs of displaced dipolar elements that make up the present invention.

The four arrangements of pairs of displaced dipolar elements used in this experiment were as follows:

Type ETP000 was a form of the present invention is which a parallel linear array of common pole pairs of 250 gauss peak flux with a centre to centre spatial separation of 2 mm.

Type ETP006 was a combination of two intersecting parallel linear common pole arrays at 90 degrees orientation to each other having a peak magnetic flux of 300 gauss and a spatial separation between pairs of 3.5 mm.

Type ETP008 was a parallel linear array of common pole pairs of 450 gauss peak flux with a centre to centre spatial separation of 4 mm.

Type ETP011 was a combination of two intersecting parallel linear common pole arrays at 90 degrees orientation to each other having a peak magnetic flux of 150 gauss and a spatial separation between pairs of 3 mm.

Figure 13:
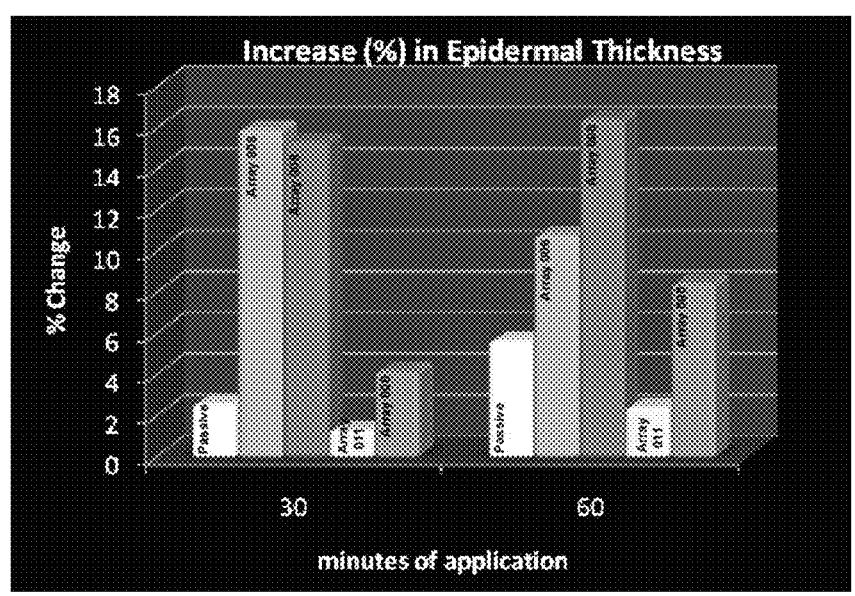
FIG. 13 is a graph of the relative change in epidermal thickness caused by the humectant urea when delivered into the skin by various forms of the present magnetic array invention when compared to normal topical application (passive).

FIG. 13 shows the results of changes in epidermal thickness in response to the penetration of Urea into human epidermal tissues. The segment marked Passive indicted the normal changes in epidermal thickness in response to topical and occluded application of a Urea Gel. This is considered the control.

Type 011 arrangement of the present invention had the effect of decreasing normal penetration, while the configurations of Type ETP000, ETP006 and ETP008 enhanced penetrations to different degrees over time.

Example 4

Materials

1) Mineral oil and a solution of Curcumin in mineral oil (0.5% w/w).
2) 35 mm×35 mm segments of ETP008 and ETP012 magnetic materials; ETP008 being a parallel linear array of common pole pairs of 450 gauss peak flux with a centre to centre spatial separation of 4 mm; ETP012 being an oriented displaced dipolar magnetic element array created by drawing a secondary flux pattern over a linear pattern comprising 2.0 mm poles, creating a pair of displaced dipolar magnetic elements of pitch of 2.5 pairs per centimeter, with the inter-pair flux gradient being 700 gauss or 1750 gauss per centimeter and the secondary field elements being oriented at 90 degrees to the primary and consisting of parallel pairs of displaced dipolar magnetic elements of pitch of 1.5 mm, creating 3.5 pairs per centimeter, with 300 gauss per centimeter oriented flux.
3) 35 mm×35 mm segments of a "passive" non-magnetic material which is identical to the active materials in all respects except for the presence of the magnetic field.
4) Six healthy human subjects between the ages of 20 and 40.
5) Multi-Photon Microscopy apparatus and computer software capable of processing Multi-Photon microscopy images.

Figure 14:
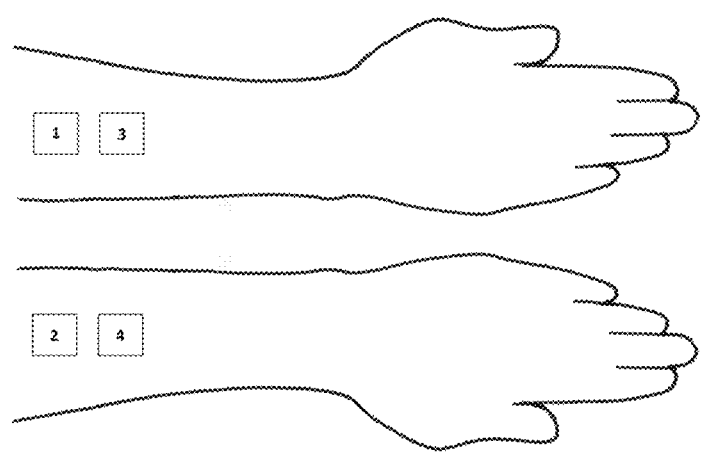
FIG. 14 is a schematic of the volar forearm showing the placement of test samples: (1) mineral oil only (control), (2) mineral oil in the presence of the magnetic material, (3) curcumin in mineral oil in the presence of the magnetic material and (4) curcumin in mineral oil in the presence of the passive non-magnetic material.

Test Procedure:
1) The test samples of mineral oil alone (vehicle) or mineral oil containing Curcumin were applied to the volar forearm region skin of both arms of each subject, with the samples being applied either alone, in the presence of the magnetic materials, or in the presence of the "passive" non-magnetic material in the following manner: (1) mineral oil only (control); (2) mineral oil in the presence of the magnetic material; (3) curcumin in mineral oil in the presence of the magnetic material; and (4) curcumin in mineral oil in the presence of the passive non-magnetic material (as described in FIG. 14).
2) After an application period of one hour, the test samples were removed and the region of skin directly below the test sample application was imaged with the MPM apparatus.
3) Images of the skin structure were taken at 5 µm below the skin surface and then at intervals of 5 µm to a depth of at least 40 µm below the skin surface.

Figure 15:
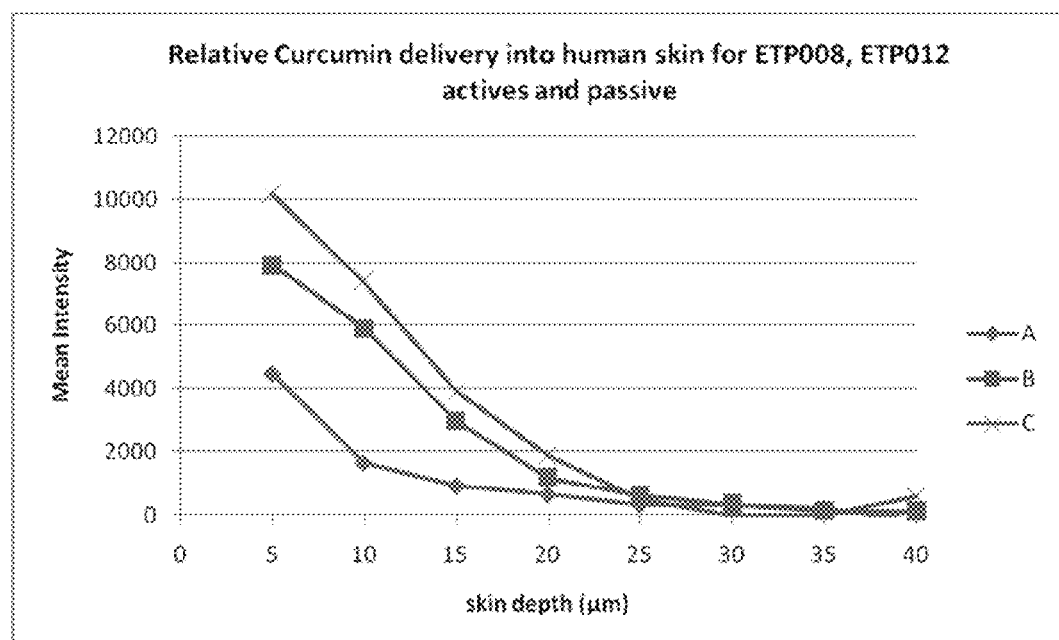
FIG. 15 is a graph of the relative delivery of Curcumin into human skin for (A) passive, (B) ETP008 and (C) ETP012 delivery.

Data Treatment:
1) All images generated were converted to grey-scale images.
2) The grey-scale images were then analysed using a suitable software (SPCimage) and a mean intensity value determined for a fixed image area (100×100 µm).
3) Mean intensity data for the applications of mineral oil only in the presence of the magnetic material or in the presence of the "passive" material at each depth below the skin surface, were used as the background intensity data and were subtracted from the mean intensity data for Curcumin in mineral oil applications in the presence of the magnetic material or "passive" material for each appropriate depth.
4) Results were expressed as plots of the mean intensity as a function of skin depth (µm) as shown in FIG. 15.

Results

Treatment of the subjects with the ETP008 and ETP012 magnetic material results in a significant increase in Curcumin concentrations in the skin when compared with application in the presence of the "passive" material.

Example 5

Materials 1) 5% w/w urea in VersaBase Gel (PCCA, Huston, Tex.).
2) 11 mm diameter discs of flexible magnetic array matrix (ETP008) material and "passive" non-magnetic material which are identical to the active materials in all respects except for the presence of the magnetic field.
3) Passive occlusive material consisting of a polymer film of similar thickness and cut to the same dimensions as the active magnetic polymer material.
4) Epidermal membranes obtained from human skin sourced from abdominal region following abdominoplasty surgery.
5) Pyrex glass Franz-type diffusion cells (enabling permeation across epidermal membranes of cross sectional area approximately 1.18 cm$^2$); receptor volume approximately 3.5 mL.
6) Phosphate buffered saline (PBS).

7) Thermostatted water bath with magnetic stirring capability.
8) DMAB reagent (4% w/v) prepared with conc. sulphuric acid (4% v/v) in alcohol (95%).
9) Digital portable LCR meter (TH2821/A/B, Changzhou Tonghui Electronic Co., Ltd, China).

Method

Preparation of Epidermal Membranes

Epidermal membranes were obtained by the heat separation method (Kligman & Christophers, 1963 Preparation of isolated sheets of human stratum corneum. *Arch. Dermatol.* 88: 70-73).

In Vitro Diffusion Studies
1) The membrane was placed between the donor and receptor compartment of the cell and allowed to equilibrate for 1 h with PBS in the receptor compartment which was stirred continuously with a magnetic stirrer.
2) PBS was placed in the donor (1 mL) and receptor (approx. 3.5 mL) compartments of the cell which were then placed in a water bath maintained at 37±0.5° C.
3) Epidermal membrane integrity was determined by visual inspection over a bright light and electrical resistance (kΩ) measurements using a digital portable LCR meter (TH2821/A/B, Changzhou Tonghui Electronic Co., Ltd, China). The measurements were taken by immersing the stainless steel probe lead tips, one each in the donor and receptor compartments (Fasano et al, 2002 Rapid integrity assessment of rat and human epidermal membranes for in vitro dermal regulatory testing: correlation of electrical resistance with tritiated water permeability. *Toxicol. In Vitro* 16: 731-40). Membranes exhibiting an electrical resistance less than 20 kΩ were rejected from the study.
4) The diffusion cells were emptied and the receptor compartments refilled with fresh preheated PBS at 37±0.5° C.
5) Urea gel (0.5 g) was placed in the donor compartment of each cell.
6) Sections of magnetic film array were inserted into the donor compartment of the Franz type cell and suspended above and exterior to the gel, whilst passive cells had non-magnetic polymer film of similar dimensions placed above the gel.
7) All cells were also occluded by sealing the top of the donor compartment of the cell with Parafilm.
8) Aliquots from the receptor phase were withdrawn from the sampling arm and replaced with fresh pre-heated (at 37° C.) PBS over a 2 h period.
9) The total urea content permeating the epidermal membrane to the receptor solution samples obtained from individual experiments was determined by spectroscopic analysis.
10) At time 2 h the donor and receptor fluids were recovered, the cell disassembled and the skin epidermal membrane examined for obvious tears (any cells with torn membranes were rejected).

Spectroscopic Analyses:

Urea quantification was based on the analytical method of Knorst et al 1997 (Analytical methods for measuring urea in pharmaceutical formulations. *J. Pharm. Biomed. Anal.* 15: 1627-32), a modified derivatisation by p-dimethylaminobenzaldehyde (DMAB) to convert urea into a coloured compound.

Derivatisation of urea in skin diffusate employed equal volumes of sample solution and the DMAB reagent (4% w/v) which was prepared with conc. sulphuric acid (4% v/v) in alcohol (95%). In this case 200 μL of the urea sample was mixed with 200 μL of the DMAB reagent. After 10 min the absorbance of the coloured derivatised solution was measured at 420 nm using a UVmini-1240 UV-Vis spectrophotometer (Shimadzu Scientific Instruments) against an appropriate reagent blank (receptor solution processed as for skin permeation receptor solution samples). Spectrophotometric analysis was carried out for quantitative analysis of urea that permeated the skin. All calibration curves of urea standards showed good linearity in the concentration range of 7.8-125 μg/mL ($r^2$=0.99; n=5). The limit of detection (LOD) and limit of quantitation (LOQ) of the assay were 0.83 and 2.5 μg/mL respectively.

Data Treatment:

The results were compiled from nine cells containing the magnetic array film and eight control cells containing the passive non-magnetic film. A comparison of the cumulative amount of urea penetrating the epidermis to the receptor solution (μg/cm$^2$) versus time (mins) was plotted for passive and magnetic array enhanced applications (FIG. 16).

Results

Figure 16:
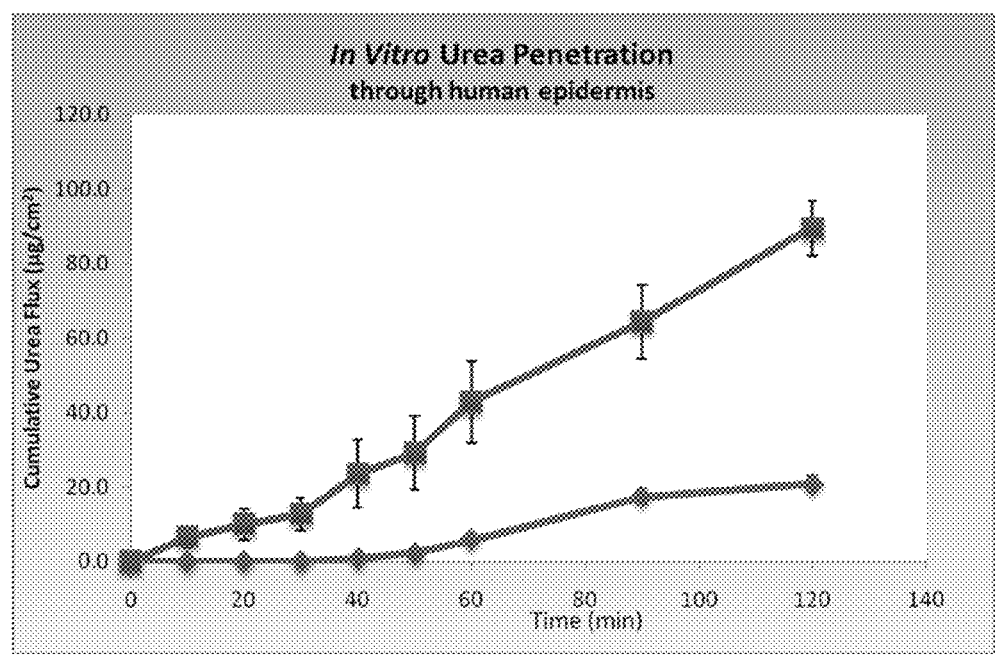
FIG. 16 is a graph of the cumulative amount of urea ($\mu g/cm^2$) permeating human epidermis to the receptor compartment during application of 5% urea gel in the presence of magnetic material ETP008 (squares) verses non-magnetic passive material (diamonds).

The in vitro permeation profiles of urea across human epidermis are presented in FIG. 16.

There was a significant increase in the mean cumulative permeation of urea over 2 h for samples in the presence of the magnetic array material (89.54±7.34 μg/cm$^2$) as compared to samples in the presence of the non-magnetic passive material (20.83±2.02 μg/cm$^2$; mean±sem; p<0.0001 unpaired t test). All permeation parameters were significantly enhanced by the presence of the magnetic material (based on unpaired t tests). The lag time was reduced from 40.58±3.98 to 21.13±6.27 min (p<0.02), whilst steady state flux increased from 0.24±0.03 to 0.75±0.06 μg/cm$^2$·min (p<0.0001) by administration of urea with the magnetic film array.

Numerous variations and modifications will suggest themselves to persons skilled in the relevant technical arts, in addition to those already described, without departing from the basic inventive concepts. All such variations and modifications are to be considered within the scope of the present invention, the nature of which is to be determined from the foregoing description.

The claims defining the invention are as follows:

1. A method for delivering a skin care active agent comprising:
applying an active agent(s) between a target dermal barrier and a magnetic device, the magnetic device comprising at least a first set of pairs of displaced dipolar magnetic elements and a second set of pairs of displaced dipolar magnetic elements,
wherein pairs of displaced dipolar magnetic elements in the first set of pairs of displaced dipolar magnetic elements have surfaces linked by a magnetic return and pairs of displaced dipolar magnetic elements in the second set of pairs of displaced dipolar magnetic elements have surfaces linked by a magnetic return,
wherein the magnetic return is orientated on surfaces of the pairs of displaced dipolar magnetic elements distal to the dermal barrier,
wherein the first set of pairs of displaced dipolar magnetic elements form a first spatial layer and wherein the second set of pairs of displaced dipolar magnetic elements forms a separate, second spatial layer relative to the first set of pairs of displaced dipolar magnetic elements,
wherein the spatial layers are arranged such that the first spatial layer is stacked on the target dermal barrier and the second spatial layer is stacked on top of the first layer, distal to the barrier, wherein alignment of the first spatial layer comprising the first set of pairs of displaced dipolar magnetic elements is angularly offset between 45° and 90° relative to the second spatial layer comprising the second set of pairs of displaced dipolar magnetic elements, and wherein the angular offset of the first spatial layer comprising the first set of pairs of displaced dipolar magnetic elements relative to the second spatial layer comprising the second set of pairs of displaced dipolar magnetic elements results in multiple intersections of magnetic fields and multiple regions of magnetic flux gradient, wherein magnetic flux of each magnetic pole of the pairs of displaced dipolar magnetic elements is between 100 Gauss and 600 Gauss, and wherein magnetic poles of the pairs of displaced dipolar magnetic elements in a spatial region are between 1.0 mm and 5.0 mm apart, and moving in a reciprocal or rotational manner the magnetic device so that active agents in proximity to said device will be subject to alternating polarities of magnetic field and alternating magnetic flux gradients in response to said reciprocal or rotational movement.

2. The method according to claim 1 wherein the magnetic device includes an electronic or mechanical means for moving the magnetic device over the dermal barrier.

3. The method according to claim 2 wherein the movement of the magnetic device has an oscillation frequency of 1 Hz to 5 Hz and the strength of the magnet field produced by each magnetic element is between 100 and 500 Gauss.

4. The method according to claim 2 wherein the movement of the magnetic device has an oscillation frequency of 100 to 8,000 Hz and the strength of the magnet field produced by each magnetic element is between 100 and 600 Gauss.

5. The method according to claim 1 wherein each pair of displaced dipolar magnetic elements is disposed at a repetition rate of between 2 and 10 dipolar pairs per centimeter.

6. The method according to claim 1 wherein each pair of displaced dipolar magnetic elements is disposed at a repetition rate of between 1.5 and 4 dipolar pairs per centimeter.

7. The method according to claim 1 wherein the magnetic flux of each magnetic pole is 125 to 450 Gauss.

8. The method according to claim 1 wherein a delta magnetic flux between two adjacent poles of opposite polarity is between 100 Gauss and 2000 Gauss.

9. The method according to claim 8 wherein the delta magnetic flux between two adjacent poles of opposite polarity is 200 to 900 Gauss.

10. The method of claim 1 wherein the device is in the form of one of the following: a brush, a pad, a roller applicator, or a pen device.

11. The method of claim 1 wherein the active agent is applied to the dermal barrier prior to application of the magnetic device.

12. The method of claim 1 wherein the active agent is applied to the magnetic device prior to application of the magnetic device to the dermal barrier.

* * * * *

UNITED STATES PATENT AND TRADEMARK OFFICE
CERTIFICATE OF CORRECTION

| | | |
|---|---|---|
| PATENT NO. | : 9,463,330 B2 | |
| APPLICATION NO. | : 13/704157 | |
| DATED | : October 11, 2016 | |
| INVENTOR(S) | : Jeffrey D. Edwards | |

It is certified that error appears in the above-identified patent and that said Letters Patent is hereby corrected as shown below:

In the Specification

At Column 10, Line 22, "magnet field" should be -- magnetic field --.

In the Claims

At Column 23, Line 8, "elements, and" should be -- elements, --.

At Column 24, Line 1, "magnet field" should be -- magnetic field --.

At Column 24, Line 1, "magnet field" should be -- magnetic field --.

Signed and Sealed this
Fourteenth Day of March, 2017

Michelle K. Lee
*Director of the United States Patent and Trademark Office*